United States Patent
Zenisek (10) Patent No.: US 12,128,241 B2
(45) Date of Patent: Oct. 29, 2024

(54) STIMULATION CYCLING ADJUSTMENTS BASED ON USER INPUT

(71) Applicant: Medtronic, Inc., Minneapolis, MN (US)

(72) Inventor: Todd D. Zenisek, Georgetown, TX (US)

(73) Assignee: Medtronic, Inc., Minneapolis, MN (US)

( * ) Notice: Subject to any disclaimer, the term of this patent is extended or adjusted under 35 U.S.C. 154(b) by 507 days.

(21) Appl. No.: 17/643,817

(22) Filed: Dec. 10, 2021

(65) Prior Publication Data

US 2023/0181914 A1  Jun. 15, 2023

(51) Int. Cl.
*A61N 1/36* (2006.01)
*A61N 1/372* (2006.01)

(52) U.S. Cl.
CPC ..... *A61N 1/37247* (2013.01); *A61N 1/36135* (2013.01); *A61N 1/36167* (2013.01)

(58) Field of Classification Search
CPC ............ A61N 1/37247; A61N 1/36135; A61N 1/36167; A61N 1/36132; A61N 1/36003; A61N 1/36007; A61N 1/36062; A61N 1/36067; A61N 1/36071; A61N 1/36082; A61N 1/36107

See application file for complete search history.

(56) References Cited

U.S. PATENT DOCUMENTS

| | | | |
|---|---|---|---|
| 7,016,730 B2 | 3/2006 | Ternes | |
| 9,089,713 B2 | 7/2015 | John | |
| 9,132,272 B2 | 9/2015 | Alves et al. | |
| 9,492,669 B2 | 11/2016 | Demmer et al. | |
| 9,623,244 B2 | 4/2017 | Kothandaraman | |
| 9,731,133 B1 | 8/2017 | Thacker et al. | |
| 10,204,706 B2 | 2/2019 | Davis et al. | |
| 10,449,371 B2 | 10/2019 | Serrano Carmona | |
| 2008/0255628 A1 | 10/2008 | Seim | |
| 2016/0114161 A1 | 4/2016 | Amblard et al. | |
| 2017/0239470 A1* | 8/2017 | Wei | A61N 1/0514 |
| 2019/0262608 A1 | 8/2019 | Whiting et al. | |
| 2022/0266028 A1* | 8/2022 | Bink | A61N 1/36171 |

OTHER PUBLICATIONS

Extended Search Report from counterpart European Application No. 23165186.0 dated Apr. 28, 2023, 5 pp.
Response to Extended Search Report dated Apr. 28, 2023, from counterpart European Application No. 22211618.8 filed Nov. 30, 2023, 16 pp.
North et al., "Spinal Cord Stimulator Adjustment to Maximize Implanted Battery Longevity: A Randomized, Controlled Trial Using a Computerized, Patient Interactive Programmer", Neuromodulation: Technology at the Neural Interface, vol. 7, Issue 1, Jan. 2004, pp. 13-25.

* cited by examiner

*Primary Examiner* — Eugene T Wu (74) *Attorney, Agent, or Firm* — Shumaker & Sieffert, P.A.

(57) ABSTRACT

A medical system includes techniques for adjusting the cycling of electrical stimulation therapy delivered by a medical device based on user input. The disclosure describes techniques to iteratively adjust the duration that stimulation is delivered and not delivered based on user input indicative of patient's symptoms.

16 Claims, 4 Drawing Sheets

STIMULATION CYCLING ADJUSTMENTS BASED ON USER INPUT

TECHNICAL FIELD

The disclosure relates to electrical stimulation therapy and more particularly to electrical stimulation therapy by portable medical devices.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), tibial stimulation and peripheral nerve stimulation (PNS).

Electrical stimulation may be delivered to a patient by the medical device in a train of electrical pulses, and parameters of the electrical pulses may include a frequency, an amplitude, a pulse width, and a pulse shape. An evoked compound action potential (ECAP) is synchronous firing of a population of neurons which occurs in response to the application of a stimulus including, in some cases, an electrical stimulus by a medical device. The ECAP may be detectable as being a separate event from the stimulus itself, and the ECAP may reveal characteristics of the effect of the stimulus on the nerve fibers.

SUMMARY

In general, the disclosure describes devices, systems, and techniques for adjusting cycling of electrical stimulation therapy delivered by a medical device. In this manner, the medical device may balance the trade-off between clinical efficacy of electrical stimulation therapy to relieve patient symptoms and the amount of electrical energy consumed to deliver the electrical stimulation therapy. For example, a system may iteratively adjust the duration of delivered therapy and verify the patient's symptoms.

In one example, this disclosure describes method comprising: causing, by processing circuitry, electrical stimulation circuitry of an implantable medical device (IMD) to output electrical stimulation therapy to a patient via electrodes implanted near a target nerve of the patient, wherein the electrical stimulation therapy is defined by parameters, the parameters comprising ON-time and OFF-time; incrementing, by the processing circuitry, the OFF-time by a first duration; receiving, by the processing circuitry, input via a user interface operatively coupled to the processing circuitry, the input describing the state of symptoms of the patient, wherein the electrical stimulation therapy is configured to relieve the symptoms; responsive to receiving input that the symptoms of the patient have not returned incrementing, by the processing circuitry, the OFF-time again by the first duration; responsive to receiving input that the symptoms of the patent have returned: decreasing, by the processing circuitry, the OFF-time by a second duration; and receiving, by the processing circuitry, input via the user interface describing the state of symptoms of the patient. After decreasing the OFF-time by the second duration and responsive to receiving input that the symptoms of the patient have returned decreasing, by the processing circuitry, the OFF-time again by the second duration.

In another example, this disclosure describes a system comprising: an electrical lead comprising one or more electrodes in contact with tissue of a patient; a user interface configured to receive input from a user; an implantable medical device comprising: an electrical connector configured to connect to the electrical lead; electrical stimulation circuitry configured to output electrical stimulation therapy to a patient via the one or more electrodes, wherein the electrical stimulation therapy is configured to relieve symptoms of the patient. The system further includes processing circuitry configured to: cause the electrical stimulation circuitry to output electrical stimulation therapy to a patient wherein the electrical stimulation therapy is defined by parameters, the parameters comprising ON-time and OFF-time; increment the OFF-time by a first duration; receive input via the user interface, the input describing the state of symptoms of the patient; responsive to receiving input that the symptoms of the patient have not returned increment the OFF-time again by the first duration; responsive to receiving input that the symptoms of the patent have returned: decrease the OFF-time by a second duration; and receive input via the user interface describing the state of symptoms of the patient; after decreasing the OFF-time by the second duration and responsive to receiving input that the symptoms of the patient have returned decrease the OFF-time again by the second duration.

In another example, this disclosure describes a non-transitory computer-readable storage medium comprising instructions that, when executed, cause one or more processors of a computing device to: cause electrical stimulation circuitry of an implantable medical device to output electrical stimulation therapy to a patient wherein: the electrical stimulation therapy is defined by parameters, the parameters comprising ON-time and OFF-time, and wherein the electrical stimulation therapy is configured to relieve symptoms of the patient; increment the OFF-time by a first duration; receive input via a user interface, the input describing the state of symptoms of the patient; responsive to receiving input that the symptoms of the patient have not returned increment the OFF-time again by the first duration; responsive to receiving input that the symptoms of the patent have returned: decrease the OFF-time by a second duration; and receive input via the user interface describing the state of symptoms of the patient; after decreasing the OFF-time by the second duration and responsive to receiving input that the symptoms of the patient have returned decrease the OFF-time again by the second duration.

The details of one or more examples of the disclosure are set forth in the accompanying drawings and the description below. Other features, objects, and advantages of the disclosure will be apparent from the description and drawings, and from the claims.

DETAILED DESCRIPTION

The devices, systems, and techniques of this disclosure relate to a medical device setup procedure that enables a system to semi-automatically find a stimulation ON time and stimulation OFF time, or adjust those times, to determine a medical device programmed configuration that may reduce the amount of energy consumed while maintaining efficacious therapy for a particular patient. Increasing the duration of the time OFF and decreasing the duration of the time ON may use less battery capacity, but may result in patient discomfort if stimulation is delivered for an inadequate amount of time that enables symptoms to return.

Using an external computing device, e.g., a medical device programmer, the healthcare provider (HCP) or the patient, may start the setup procedure via a user interface. Processing circuitry of the external computing device may start by automatically changing the configuration of the implantable medical device (IMD) by programming a first ON interval duration and a first OFF interval duration. The algorithm may be semi-automatic in examples where the system will pause while waiting for a response from the patient. In other examples, processing circuitry of the IMD may execute the steps of the algorithm, rather than receiving updated programming commands from the external computing device.

The processing circuitry may re-program the IMD to increase the time OFF by a preset amount, pausing for each trial, until the patient reports that the symptom breakthrough, e.g., the symptoms, such as pain, become noticeable. The processing circuitry may then reduce the time OFF to the pain-free setting (or at least pain reduced, depending on the patient). Then the processing circuitry may perform similar trials by reducing the electrical stimulation time ON in specified increments, pausing for each trial, until the patient reports symptom breakthrough, e.g., feeling more pain than if the electrical stimulation was reducing the pain. The processing circuitry may then increase the time ON to the pain-free or pain-reduced setting. This disclosure will focus on electrical stimulation therapy to relieve pain, to simplify the description. However, pain reduction is just one example of a patient symptom. The techniques of this disclosure apply equally to other symptoms, such as incontinence, epilepsy symptoms, Parkinson's tremors, gait issues. In the example of a cardiac device, symptoms may include bradycardia, reduced or increased blood flow as measured by an echocardiogram, and so on.

The techniques of this disclosure may apply to any portable device, e.g., a device that depends on a battery or other electrical energy storage unit. For example, wearable medical devices may be worn externally, such as on a belt loop, straps or adhesive, or may be implanted in a patient. Wearable devices may include a battery to power the device, which may need to be periodically charged or replaced. In the example of an implanted device, the patient requires surgery to remove and replace the device with a new device and fresh battery. Rechargeable devices may be recharged with a power transfer device including a coil and electronics to monitor and control the recharging, as well as communicate with the medical device. For medical devices configured to deliver therapy to reduce pain and other symptoms, the medical device may deliver electrical stimulation signals, such as a series of electrical current pulses, through electrodes placed on leads implanted near nerves, such as near the spinal cord. Each patient may require a different magnitude, frequency, and other stimulation parameters based on the patient physiology, patient sensitivity as well as based on the type of device, electrodes, and where the electrodes sit relative to the target tissue, e.g., a target nerve.

In some examples, a patient, or caregiver, may run the setup procedure to set or adjust the ON and OFF times as many times as desired over the life of the medical device. Also, in some examples, the setup procedure may provide separate time durations as needed during the day. For example, the ON and OFF times may be different for daytime activity hours when compared to night sleeping hours. In some examples the OFF time may be set to a longer duration during sleep to provide greater energy savings. In some examples, the switch between the separate setting durations may be triggered by the patient, by an internal clock of the medical device, by an accelerometer to determine active times versus sleep times, and so on.

Figure 1:
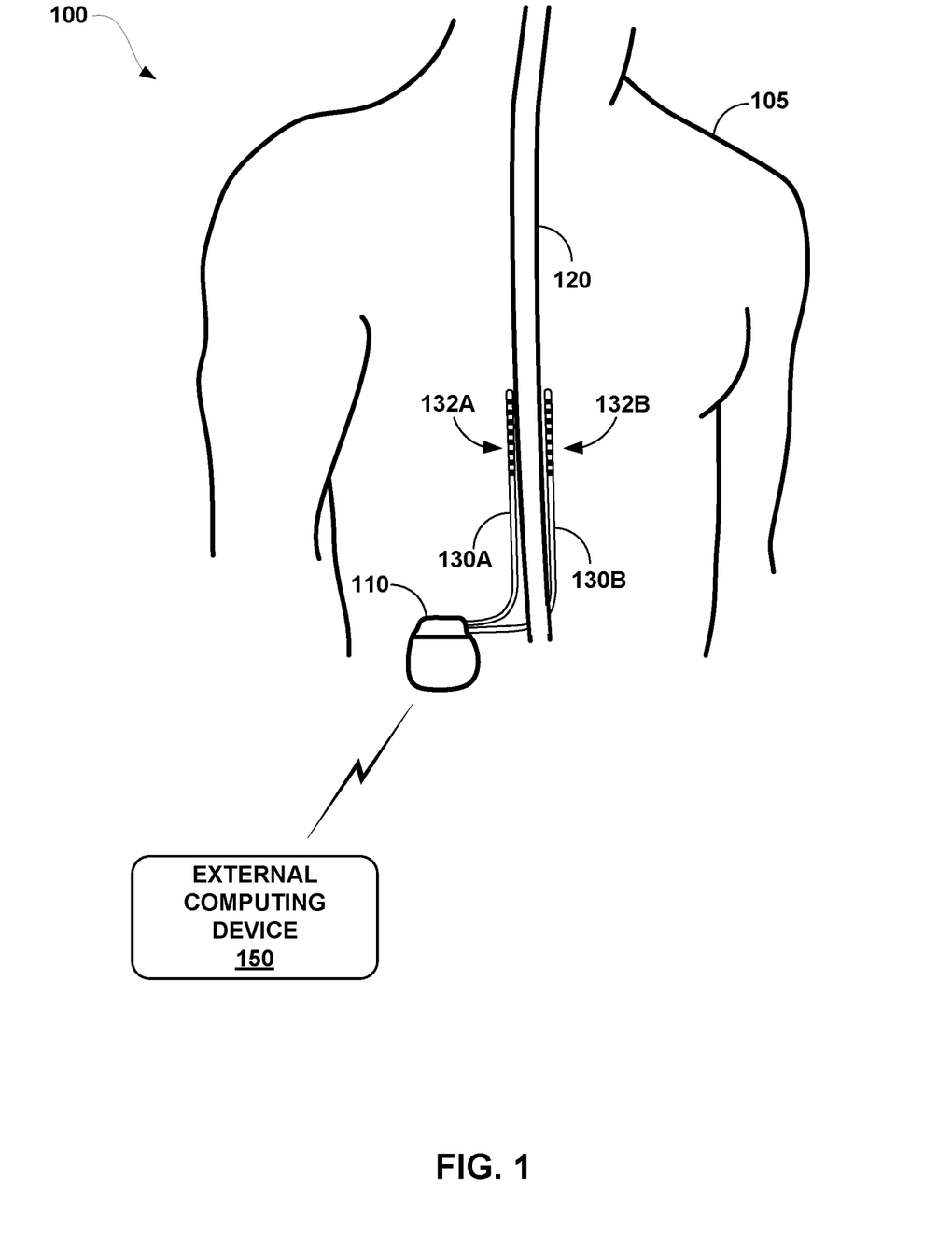
FIG. 1 is a conceptual diagram illustrating an example system that includes an implantable medical device (IMD) configured to deliver spinal cord stimulation (SCS) therapy and an external programmer, in accordance with one or more techniques of this disclosure.

FIG. 1 is a conceptual diagram illustrating an example system 100 that includes an IMD 110 configured to deliver spinal cord stimulation (SCS) therapy and an external computing device 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in FIG. 1, system 100 includes an IMD 110, leads 130A and 130B, and external computing device 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of electrodes of leads 130A and/or 130B (collectively, "leads 130"), e.g., for relief of chronic pain or other symptoms. In other examples, IMD 110 may be coupled to a single lead carrying multiple electrodes or more than two leads each carrying multiple electrodes. IMD 110 may include an electrical connector configured to connect to the electrical leads, e.g., in the header of IMD 110. In some examples, the stimulation signals, or pulses, may be configured to elicit detectable ECAP signals that IMD 110 may use to determine the posture state occupied by patient 105 and/or determine how to adjust one or more parameters that define stimulation therapy. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

This disclosure will focus on a device used for spinal cord stimulation, as shown in the example of FIG. 1 to simplify the description. However, the techniques of this disclosure may also apply to other devices, including wearable devices, that may be located elsewhere on patient 105. Some examples may include devices located near the head for DBS, near the tibial region, near the heart for cardiac therapy and/or monitoring, and so on.

In other words, although in one example IMD 110 takes the form of an SCS device, in other examples, IMD 110 takes the form of any combination of deep brain stimulation (DBS) devices, implantable cardioverter defibrillators (ICDs), pacemakers, cardiac resynchronization therapy devices (CRT-Ds), left ventricular assist devices (LVADs), implantable sensors, orthopedic devices, or drug pumps, as examples. Moreover, techniques of this disclosure may be used to determine parameters that affect stimulation thresholds (e.g., perception thresholds and detection thresholds) associated any one of the aforementioned IMDs and then use a stimulation threshold to inform the intensity (e.g., stimulation levels) of therapy. For example, changing stimulation parameters such as the number of pulses in a burst, the number of bursts over a duration, the pulse width of a pulse in a burst, the ON-time, the OFF-time, a pattern of pulses over a duration and other parameters may change the intensity as well as the efficacy of the therapy to relieve the symptoms.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a lead 130 and/or at other positions at intermediate points along the lead. Leads 130 may be implanted and coupled to IMD 110. The electrodes may transfer electrical stimulation generated by an electrical stimulation generator in IMD 110 to tissue of patient 105. Although leads 130 may each be a single lead, lead 130 may include a lead extension or other segments that may aid in implantation or positioning of lead 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes 132A and 132B of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes 132A and 132B via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

The stimulation parameter set of a therapy stimulation program that defines the stimulation pulses of electrical stimulation therapy by IMD 110 through the electrodes of leads 130 may include information identifying which electrodes have been selected for delivery of stimulation according to a stimulation program, the polarities of the selected electrodes, i.e., the electrode combination for the program, voltage or current amplitude, pulse frequency, pulse width, pulse shape of stimulation delivered by the electrodes. These stimulation parameters values that make up the stimulation parameter set that defines pulses may be predetermined parameter values defined by a user and/or automatically determined by system 100 based on one or more factors or user input.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

In some examples, lead 130 includes one or more sensors configured to allow IMD 110 to monitor one or more parameters of patient 105, such as patient activity, pressure, temperature, or other characteristics. The one or more sensors may be provided in addition to, or in place of, therapy delivery by lead 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results.

IMD 110 is configured to generate and deliver electrical stimulation therapy to a target stimulation site within patient 105 via the electrodes of leads 130 to patient 105 according to one or more therapy stimulation programs. A therapy stimulation program defines values for one or more parameters (e.g., a parameter set) that define an aspect of the therapy delivered by IMD 110 according to that program. For example, a therapy stimulation program that controls delivery of stimulation by IMD 110 in the form of pulses may define values for voltage or current pulse amplitude, pulse width, pulse rate (e.g., pulse frequency), electrode combination, pulse shape, etc. for stimulation pulses delivered by IMD 110 according to that program. In some examples, parameters may include sequences of pulses, for example a "burst" of pulses with gradually increasing current magnitudes, or some other sequence. In some examples, IMD 110 may deliver therapy for a given duration and stop delivering therapy for a given duration. In other words, parameters of the electrical stimulation therapy may include an ON-time and an OFF-time. In some examples, an ON-time may be a few seconds or minutes and the OFF-time may also be for a few seconds or minutes. The ON-time may be equal to the OFF-time in some examples, while in other examples the ON-time and the OFF-time may be different durations.

The time durations may be patient specific and vary considerably as each patient is slightly different. Some examples of possible cycling patterns may include: one minute ON/one minute OFF, five minutes ON/one minute OFF, one minute ON/20 seconds OFF, and so on.

In other examples, the time durations may be based on a ratio of ON time to OFF time, rather a specific duration. In one example implementation, the programmer may present ratio-based choices and then auto-learn the ratio as the patient changes the initial preset algorithm. In some examples, the setup procedure executing by processing circuitry of system 100 (e.g., processing circuitry of IMD 110, external computing device 150, or some combination of each) may then either recommend or present ON/OFF durations that meet that same ratio. For example, as the user is conducting the setup procedure, the system may identify that one of a 1:1, 1:2, 1:3 ratio, and so on may be working best for the patient. The system may then change its algorithm to utilize those ratio the patient has identified. That is, ff the patient trial is showing that 1:1 ratios are working best for the patient, the processing circuitry of the system may change the preset trial algorithm to ratios such as: 1 sec ON/1 sec off, 2sec ON/2OFF, 1min ON/1 Min off and so on. In this manner, the system may learn and suggest new ON/OFF patterns that meet the needs of the patient.

Furthermore, IMD 110 may be configured to deliver control stimulation to patient 105 via a combination of electrodes of leads 130, alone or in combination with an electrode carried by or defined by an outer housing of IMD 110 in order to detect ECAP signals (e.g., control pulses and/or informed pulses). The tissue targeted by the stimulation may be the same or similar tissue targeted by the electrical stimulation therapy, but IMD 110 may deliver stimulation pulses for ECAP signal detection via the same, at least some of the same, or different electrodes. Since control stimulation pulses can be delivered in an interleaved manner with informed pulses (e.g., when the pulses configured to contribute to therapy interfere with the detection of ECAP signals or pulse sweeps intended for posture state detection via ECAP signals do not correspond to pulses intended for therapy purposes), a clinician and/or user may select any desired electrode combination for informed pulses. Like the electrical stimulation therapy, the control stimulation may be in the form of electrical stimulation pulses or continuous waveforms. In one example, each control stimulation pulse may include a balanced, bi-phasic square pulse that employs an active recharge phase. However, in other examples, the control stimulation pulses may include a monophasic pulse followed by a passive recharge phase. In other examples, a control pulse may include an imbalanced bi-phasic portion and a passive recharge portion. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. The control pulses may elicit an ECAP signal from the tissue, and IMD 110 may sense the ECAP signal via two or more electrodes on leads 130. In cases where the control stimulation pulses are applied to spinal cord 120, the signal may be sensed by IMD 110 from spinal cord 120.

IMD 110 can deliver control stimulation to a target stimulation site within patient 105 via the electrodes of leads 130 according to one or more ECAP test stimulation programs. The one or more ECAP test stimulation programs may be stored in a storage device of IMD 110. Each ECAP test program of the one or more ECAP test stimulation programs include values for one or more parameters that define an aspect of the control stimulation delivered by IMD 110 according to that program, such as current or voltage amplitude, pulse width, pulse frequency, electrode combination, ON-time, OFF-time and, in some examples, timing based on informed pulses to be delivered to patient 105. In some examples, the ECAP test stimulation program may also define the number of pules and parameter values for each pulse of multiple pulses within a pulse sweep configured to obtain a plurality of ECAP signals for respective pulses in order to obtain the growth curve that IMD 110 may use to determine the current posture state of the patient. In some examples, IMD 110 delivers control stimulation to patient 105 according to multiple ECAP test stimulation programs.

A user, such as a clinician or patient 105, may interact with a user interface of an external computing device 150 to program IMD 110. In some examples, external computing device 150 may also be referred to as a programmer. Programming of IMD 110 may refer generally to the generation and transfer of commands, programs, or other information to control the operation of IMD 110. In this manner, IMD 110 may receive the transferred commands and programs from external computing device 150 to control stimulation, such as electrical stimulation therapy (e.g., informed pulses) and/or control stimulation (e.g., control pulses). For example, external computing device 150 may transmit therapy stimulation programs, ECAP test stimulation programs, stimulation parameter adjustments, therapy stimulation program selections, ECAP test program selections, user input, or other information to control the operation of IMD 110, e.g., by wireless telemetry or wired connection.

In some cases, external computing device 150 may be characterized as a physician or clinician programmer if it is primarily intended for use by a physician or clinician. In other cases, external computing device 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy, or when a patient perceives stimulation being delivered. In general, a physician or clinician programmer may support selection and generation of programs by a clinician for use by IMD 110, whereas a patient programmer may support adjustment and selection of such programs by a patient during ordinary use. In other examples, external computing device 150 may include, or be part of, an external charging device that recharges a power source of IMD 110. In this manner, a user may program and charge IMD 110 using one device, or multiple devices.

As described herein, information may be transmitted between external computing device 150 and IMD 110. Therefore, IMD 110 and external computing device 150 may communicate via wireless communication using any techniques known in the art. Examples of communication techniques may include, for example, radiofrequency (RF) telemetry and inductive coupling, but other techniques are also contemplated. In some examples, external computing device 150 includes a communication head that may be placed proximate to the patient's body near the IMD 110 implant site to improve the quality or security of communication between IMD 110 and external computing device 150. Communication between external computing device 150 and IMD 110 may occur during power transmission or separate from power transmission.

In some examples, IMD 110, in response to commands from external computing device 150, delivers electrical stimulation therapy according to a plurality of therapy stimulation programs to a target tissue site of the spinal cord 120 of patient 105 via electrodes 132 on leads 130. In some examples, IMD 110 modifies therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

In the example of FIG. 1, IMD 110 described as performing a plurality of processing and computing functions. However, external computing device 150 instead may perform one, several, or all of these functions. In this alternative example, IMD 110 functions to relay sensed signals to external computing device 150 for analysis, and external computing device 150 transmits instructions to IMD 110 to adjust the one or more parameters defining the electrical stimulation therapy based on analysis of the sensed signals. For example, IMD 110 may relay the sensed signal indicative of an ECAP to external computing device 150. External computing device 150 may compare the parameter value of the ECAP to the target ECAP characteristic value, and in response to the comparison, external computing device 150 may instruct IMD 110 to adjust one or more stimulation parameter that defines the electrical stimulation informed pulses and, in some examples, control pulses, delivered to patient 105.

After initially implanting IMD 110 in patient 105, a caregiver, e.g., the health care provider, may determine the parameters that will relieve the symptoms for patient 105, e.g., reduce or eliminate pain, tremors, and so on. Using a user interface for external computing device 150, the caregiver may select various parameters, such as pulse magnitude, pulse width, burst type, pulse shape, ON-time, OFF-time and so on. The caregiver may use external computing device 150 to send instructions to program IMD 110 to operate using the selected parameters. In this disclosure, ON-time refers to when IMD 10 is operating to deliver electrical stimulation therapy, such as one or more pulse trains. OFF-time refers to when IMD 10 withholds delivery, e.g., of the one or more pulse trains. In some examples, during OFF-time IMD 10 may cease all stimulation delivery.

Using user interface of external computing device 150, a user may start the procedure to balance clinical efficacy, e.g., to relieve symptoms of patient 105, with reducing battery consumption. Reduced battery consumption may be an advantage for patient 105 because reducing battery usage may mean longer times between recharge cycles or longer times between device replacement for non-rechargeable devices with a primary cell. The system of this disclosure may also provide other advantages, such as reduce time demand for the health care provider while at the same time allows the patient control of the system to set the parameters specific to the patient. The system of this disclosure may also allow the patient so change the ON/OFF cycling parameters any time the patient may want.

Processing circuitry of system 100 may cause electrical stimulation circuitry of an implantable medical device (IMD), to output electrical stimulation therapy to a patient via electrodes implanted near target tissue of the patient 105, e.g., a target nerve, muscle tissue, and so on. As described above, the electrical stimulation therapy may be defined by various parameters including ON-time and OFF-time. A reduced ON-time and increased OFF-time may reduce battery consumption.

Processing circuitry of system 100 may increment the OFF-time by a first predetermined duration. The new OFF-time will be the previous OFF-time, plus incremental duration. For example, the processing circuitry may increment a 30 second OFF-time by ten seconds, fifteen seconds, thirty seconds or some other duration. The processing circuitry may receive input the user interface, e.g., of external computing device 150 describing the state of symptoms of the patient. For example, patient 105 may report that increasing the OFF-time had no noticeable effect on their symptoms, in other words, increasing the OFF-time did not cause the patient's symptoms to return. In other examples, the state of the symptoms may be measurable, e.g., by measuring blood flow, heart rate, or some other biological characteristic, rather than the perception of patient 105.

Responsive to receiving input that the symptoms of the patient have not returned, the processing circuitry may again OFF-time by the predetermined duration. In some examples, the processing circuitry of external computing device 150 may perform the functions of the procedure. That is, the processing circuitry of external computing device 150 may execute instructions to receive the input describing the state of symptoms of the patient, determine whether or not a parameter needs to be changed, and re-program IMD 110 with the new parameters, e.g., via telemetry communications.

In other examples, the processing circuitry of IMD 110 may execute instructions to receive the input describing the state of symptoms of the patient and determine whether or not a parameter needs to be changed. For example, external computing device 150 may receive an indication via a user interface for computing device 150 describing the state of symptoms of the patient, e.g., symptoms returned or symptoms have not returned after adjusting a parameter. External device 150 may send the indication to IMD 110, rather than reprogramming IMD 110. Instead, processing circuitry of 1MD 110 may receive the indication describing the state of symptoms of the patient and make adjustments to the parameter, e.g., increment or decrease the OFF-time, based in programming instructions executed by the processing circuitry of IMD 110.

Responsive to receiving input that the symptoms of the patent have returned, the processing circuitry of system 100 may decrease the OFF-time by a predetermined second duration. In some examples, the second duration may be less than the first duration. For example, the processing circuitry may iteratively adjust the OFF-time in, e.g., twenty-second increments, for each test cycle until the processing circuitry receives an indication that the patient's symptoms have returned. Then the processing circuitry may iteratively decrease the OFF-time in smaller increments, e.g., in five-second or ten-second increments for each test cycle until the therapy begins to relieve the patient's symptoms again. In this disclosure, a 'test cycle' may include a change in a therapy parameter, delivery of therapy under the changed parameters, and checking for whether or not the patient's symptoms have returned, e.g., by asking the patient, or by taking a measurement, as described above. In other words, the processing circuitry of system 100 may receive input via the user interface describing the state of symptoms of the patient, and after decreasing the OFF-time by the second duration and responsive to receiving input that the symptoms of the patient have returned, the processing circuitry may decrease the OFF-time again by the second duration.

Once the OFF-time is set such that the therapy relieves the patient's, the processing circuitry of system 100 may perform a similar procedure by iteratively adjusting the ON-time parameter. In other words, after decreasing the OFF-time by the second duration and responsive to receiving input that the symptoms of the patient have not returned, the processing circuitry may decrease the ON-time by a third duration, e.g., ten-second, thirty-second, five-minute or some other duration. In some examples, the third duration to decrease the ON-time may be the same duration used to increase the OFF-time, described above.

Similar to adjusting the OFF-time parameter, the processing circuitry may receive input via the user interface describing the state of symptoms of the patient, and responsive to receiving input that the symptoms of the patient have not returned, for the next test cycle, the processing circuitry may again decrease the ON-time by the predetermined duration. For a test cycle in which the processing circuitry of system 100 receives an input that the symptoms of the patent have returned, the processing circuitry may increment the ON-time by a fourth duration. In some examples, the fourth duration may be less than or equal to the third duration, e.g., the processing circuitry may increment the ON-time by one-third, one-half etc. of the duration used to decrease the ON-time. The processing circuitry my increase the ON-time until the delivered therapy begins relieving the patient's symptoms. In other words, after incrementing the ON-time by the fourth duration and after receiving input that the symptoms of the patient have not returned, the processing circuitry may cause the electrical stimulation circuitry to output the electrical stimulation therapy according to the determined parameters. In the example techniques described in this disclosure, the instructions executed by the processing circuitry may cause system 100 to execute several test cycles, gradually increasing the OFF-time, then gradually decreasing the ON-time to ensure IMD 110 delivers electrical stimulation therapy without using energy that does not maintain or improve clinical efficacy. Such a procedure may deliver improved patient care by reducing battery usage and extending battery life.

In some examples, IMD 110 may include the stimulation circuitry, the sensing circuitry, and the processing circuitry. However, in other examples, one or more additional devices may be part of the system that performs the functions described herein. For example, IMD 110 may include the stimulation circuitry and the sensing circuitry, but external computing device 150 or other external device may include the processing circuitry that at least determines the posture state of the patient. IMD 110 may transmit the sensed ECAP signals, or data representing the ECAP signal, to external computing device 150, for example. Therefore, the processes described herein may be performed by multiple devices in a distributed system. In some examples, system 100 may include one or more electrodes that deliver and/or sense electrical signals. Such electrodes may be configured to sense the ECAP signals. In some examples, the same electrodes may be configured to sense signals representative of transient movements of the patient. In other examples, other sensors, such as accelerometers, gyroscopes, or other movement sensors may be configured to sense movement of the patient that indicates the patient may have transitioned to a different posture state, by which the target characteristic value may have changed accordingly.

Although in one example IMD 110 takes the form of an SCS device, in other examples, IMD 110 takes the form of any combination of deep brain stimulation (DBS) devices, implantable cardioverter defibrillators (ICDs), pacemakers, cardiac resynchronization therapy devices (CRT-Ds), left ventricular assist devices (LVADs), implantable sensors, orthopedic devices, or drug pumps, as examples. Moreover, techniques of this disclosure may be used to determine parameters that affect stimulation thresholds (e.g., perception thresholds and detection thresholds) associated any one of the aforementioned IMDs and then use a stimulation threshold to inform the intensity (e.g., stimulation levels) of therapy. For example, changing stimulation parameters such as the number of pulses in a burst, the number of bursts over a duration, the pulse width of a pulse in a burst, the ON-time, the OFF-time, a pattern of pulses over a duration and other parameters may change the intensity as well as the efficacy of the therapy to relieve the symptoms.

Figure 2:
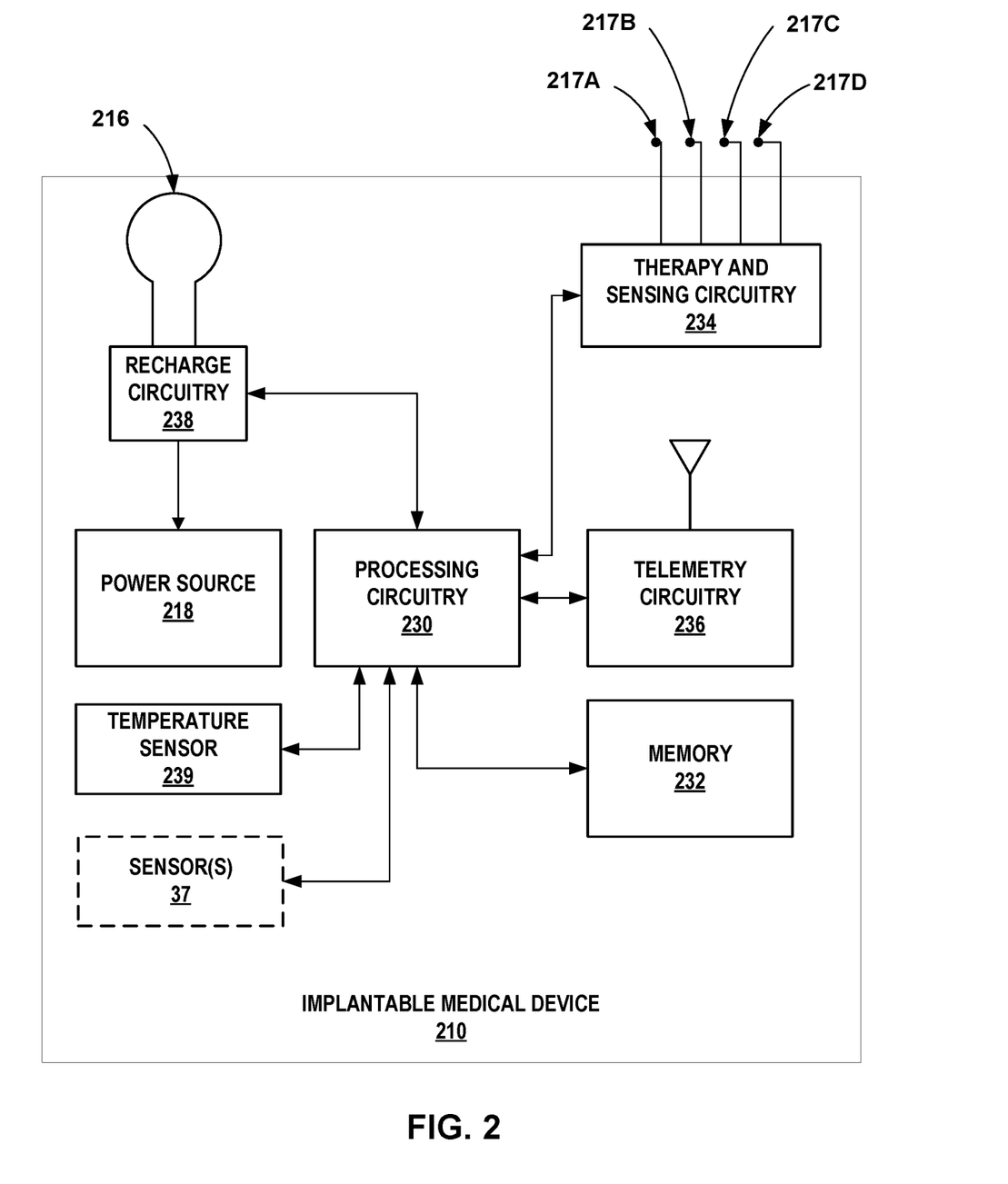
FIG. 2 is a block diagram illustrating example components of the implantable medical device of FIG. 1.

FIG. 2 is a block diagram illustrating example components of the medical device of FIG. 1. Implantable medical device 210 is an example of IMD 110 described above in relation to FIG. 1. In the example illustrated in FIG. 2, IMD 210 includes temperature sensor 239, coil 216, processing circuitry 230, therapy and sensing circuitry 234, recharge circuitry 238, memory 232, telemetry circuitry 236, power source 218, and one or more sensors 237, such as an accelerometer. In other examples, IMD 210 may include a greater or a fewer number of components, e.g., in some examples, IMD 210 may not include temperature sensor 239 or sensors 237. In general, IMD 210 may comprise any suitable arrangement of hardware, alone or in combination with software and/or firmware, to perform the various techniques described herein attributed to IMD 210 and processing circuitry 230, and any equivalents thereof.

Processing circuitry 230 of IMD 210 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 210 may include a memory 232, such as random access memory (RAM), read only memory (ROM), programmable read only memory (PROM), erasable programmable read only memory (EPROM), electronically erasable programmable read only memory (EEPROM), flash memory, comprising executable instructions for causing the processing circuitry 230 to perform the actions attributed to this circuitry. Moreover, although processing circuitry 230, therapy and sensing circuitry 234, recharge circuitry 238, telemetry circuitry 236, and temperature sensor 239 are described as separate modules, in some examples, some combination of processing circuitry 230, therapy and sensing circuitry 234, recharge circuitry 238, telemetry circuitry 236 and temperature sensor 239 are functionally integrated. In some examples, processing circuitry 230, therapy and sensing circuitry 234, recharge circuitry 238, telemetry circuitry 236, and temperature sensor 239 correspond to individual hardware units, such as ASICs, DSPs, FPGAs, or other hardware units. In this disclosure, therapy, and sensing circuitry 234 may be referred to as therapy circuitry 234, for simplicity.

Memory 232 may store therapy programs or other instructions that specify therapy parameter values for the therapy provided by therapy circuitry 234 and IMD 210. In some examples, memory 232 may also store temperature data from temperature sensor 239, instructions for recharging rechargeable power source 218, thresholds, instructions for communication between IMD 210 and an external computing device, or any other instructions required to perform tasks attributed to IMD 210. Memory 232 may be configured to store instructions for communication with and/or controlling one or more temperature sensors of temperature sensor 239.

For example, memory 232 may store programming settings for parameters such as electrical stimulation therapy output magnitude, pulse width, ON-time, OFF-time and so on. Memory 232 may determine whether a sensed bioelectrical signal is valid, such as and ECAP or other signal in response to an output electrical stimulation therapy event. Memory 232 may store programming instructions that when executed by processing circuitry 230 cause processing circuitry 230 to cause electrical stimulation circuitry therapy circuitry 234 to deliver electrical stimulation therapy to a target tissue, e.g., a target nerve of a patient.

In some examples, the programming instructions may cause processing circuitry 230 to increment the OFF-time by a first duration and receive input via the user interface, which may indicate the state of symptoms of the patient. As described above in relation to FIG. 1, in some examples processing circuitry 230 may receive the indication of whether the patient symptoms have returned after a change to a parameter and determine whether to increment or decrease the OFF-time or ON-time for each test cycle. In other examples, processing circuitry 230 may simply receive a programming instruction from, e.g., external computing device 150, to adjust the OFF-time, ON-time or other parameter during each test cycle. IMD 210 may receive the indication of the patient symptoms, and programming command to adjust therapy parameters via telemetry circuitry 236. In some examples, external computing device 150 may also communicate with processing circuitry 230 of IMD 210 inductively via coil 216 and recharge circuitry 238. In this manner, processing circuitry 230 may be described as being operatively coupled to the user interface of external device 150.

Therapy and sensing circuitry 234 may generate and deliver electrical stimulation under the control of processing circuitry 230. In some examples, processing circuitry 230 controls therapy circuitry 234 by accessing memory 232 to selectively access and load at least one of the stimulation programs to therapy circuitry 234. For example, in operation, processing circuitry 230 may access memory 232 to load one of the stimulation programs to therapy circuitry 234. In such examples, relevant stimulation parameters may include a voltage amplitude, a current amplitude, a pulse rate, a pulse width, a duty cycle, or the combination of electrodes 217A, 217B, 217C, and 217D (collectively "electrodes 217") that therapy circuitry 234 may use to deliver the electrical stimulation signal as well as sense biological signals. In other examples, IMD 210 may have more or fewer electrodes than the four shown in the example of FIG. 2. In some examples electrodes 217 may be part of or attached to a housing of IMD 210, e.g., a leadless electrode. In other examples, one or more of electrodes 217 may be part of a lead implanted in or attached to a patient to sense biological signals and/or deliver electrical stimulation, as described above in relation to FIG. 1.

In some examples, one or more electrodes connected to therapy circuitry 234 may connect to one or more sensing electrodes, e.g., attached to a housing of IMD 210. In some examples the electrodes may be configured to detect the evoked motor response caused by the electrical stimulation therapy event, or other bioelectrical signals such as ECAPs, impedance and so on.

IMD 210 also includes components to receive power to recharge rechargeable power source 218 when rechargeable power source 218 has been at least partially depleted. As shown in FIG. 2, IMD 210 includes coil 216 and recharge circuitry 238 coupled to rechargeable power source 218. Recharge circuitry 238 may be configured to charge rechargeable power source 218 with the selected power level determined by either processing circuitry 230 or an external charging device, such as external computing device 150 described above in relation to FIG. 1. Recharge circuitry 238 may include any of a variety of charging and/or control circuitry configured to process or convert current induced in coil 216 into charging current to charge power source 218.

Secondary coil 216 may include a coil of wire or other device capable of inductive coupling with a primary coil disposed external to patient 12. Although secondary coil 216 is illustrated as a simple loop of in FIG. 2, secondary coil 216 may include multiple turns of conductive wire. Secondary coil 216 may include a winding of wire configured such that an electrical current can be induced within secondary coil 216 from a magnetic field. The induced electrical current may then be used to recharge rechargeable power source 218.

Recharge circuitry 238 may include one or more circuits that process, filter, convert and/or transform the electrical signal induced in the secondary coil to an electrical signal capable of recharging rechargeable power source 218. For example, in alternating current induction, recharge circuitry 238 may include a half-wave rectifier circuit and/or a full-wave rectifier circuit configured to convert alternating current from the induction to a direct current for rechargeable power source 218. The full-wave rectifier circuit may be more efficient at converting the induced energy for rechargeable power source 218. However, a half-wave rectifier circuit may be used to store energy in rechargeable power source 218 at a slower rate. In some examples, recharge circuitry 238 may include both a full-wave rectifier circuit and a half-wave rectifier circuit such that recharge circuitry 238 may switch between each circuit to control the charging rate of rechargeable power source 218 and temperature of IMD 210. In some examples recharge circuitry 238 may also include communication circuitry.

Rechargeable power source 218 may include one or more capacitors, batteries, and/or other energy storage devices. Rechargeable power source 218 may deliver operating power to the components of IMD 210. In some examples, rechargeable power source 218 may include a power generation circuit to produce the operating power. Rechargeable power source 218 may be configured to operate through many discharge and recharge cycles. Rechargeable power source 218 may also be configured to provide operational power to IMD 210 during the recharge process. In some examples, rechargeable power source 218 may be constructed with materials to reduce the amount of heat generated during charging. In other examples, IMD 210 may be constructed of materials and/or using structures that may help dissipate generated heat at rechargeable power source 218, recharge circuitry 238, and/or secondary coil 216 over a larger surface area of the housing of IMD 210.

Although rechargeable power source 218, recharge circuitry 238, and secondary coil 216 are shown as contained within the housing of IMD 210, in alternative implementations, at least one of these components may be disposed outside of the housing. For example, in some implementations, secondary coil 216 may be disposed outside of the housing of IMD 210 to facilitate better coupling between secondary coil 216 and the primary coil of external charging device. In other examples, power source 218 may be a primary power cell and IMD 210 may not include recharge circuitry 238 and secondary coil 216, which may also be called recharge coil 216 in this disclosure.

Processing circuitry 230 may also control the exchange of information with an external computing device using telemetry circuitry 236. Telemetry circuitry 236 may be configured for wireless communication using radio frequency protocols, such as BLUETOOTH, or similar RF protocols, as well as using inductive communication protocols. Telemetry circuitry 236 may include one or more antennas configured to communicate with an external charging device, for example. Processing circuitry 230 may transmit operational information and receive therapy programs or therapy parameter adjustments via telemetry circuitry 236. Also, in some examples, IMD 210 may communicate with other implanted devices, such as stimulators, control devices, or sensors, via telemetry circuitry 236. In addition, telemetry circuitry 236 may be configured to control the exchange of information related to sensed and/or determined temperature data, for example temperatures sensed by and/or determined from temperatures sensed using temperature sensor 239. In some examples, telemetry circuitry 236 may communicate using inductive communication, and in other examples, telemetry circuitry 236 may communicate using RF frequencies separate from the frequencies used for inductive charging.

In some examples, processing circuitry 230 may transmit additional information to an external computing device related to the operation of rechargeable power source 218. For example, processing circuitry 230 may use telemetry circuitry 236 to transmit indications that rechargeable power source 218 is completely charged, rechargeable power source 218 is fully discharged, the amount of charging current output by recharge circuitry 238 e.g., to power source 218, or any other charge status of rechargeable power source 218. In some examples, processing circuitry 230 may use telemetry circuitry 236 to transmit instructions to an external charging device, including instructions regarding further control of the charging session, for example instructions to lower the power level or to terminate the charging session, based on the determined temperature of the housing/external surface of the IMD.

Figure 3:
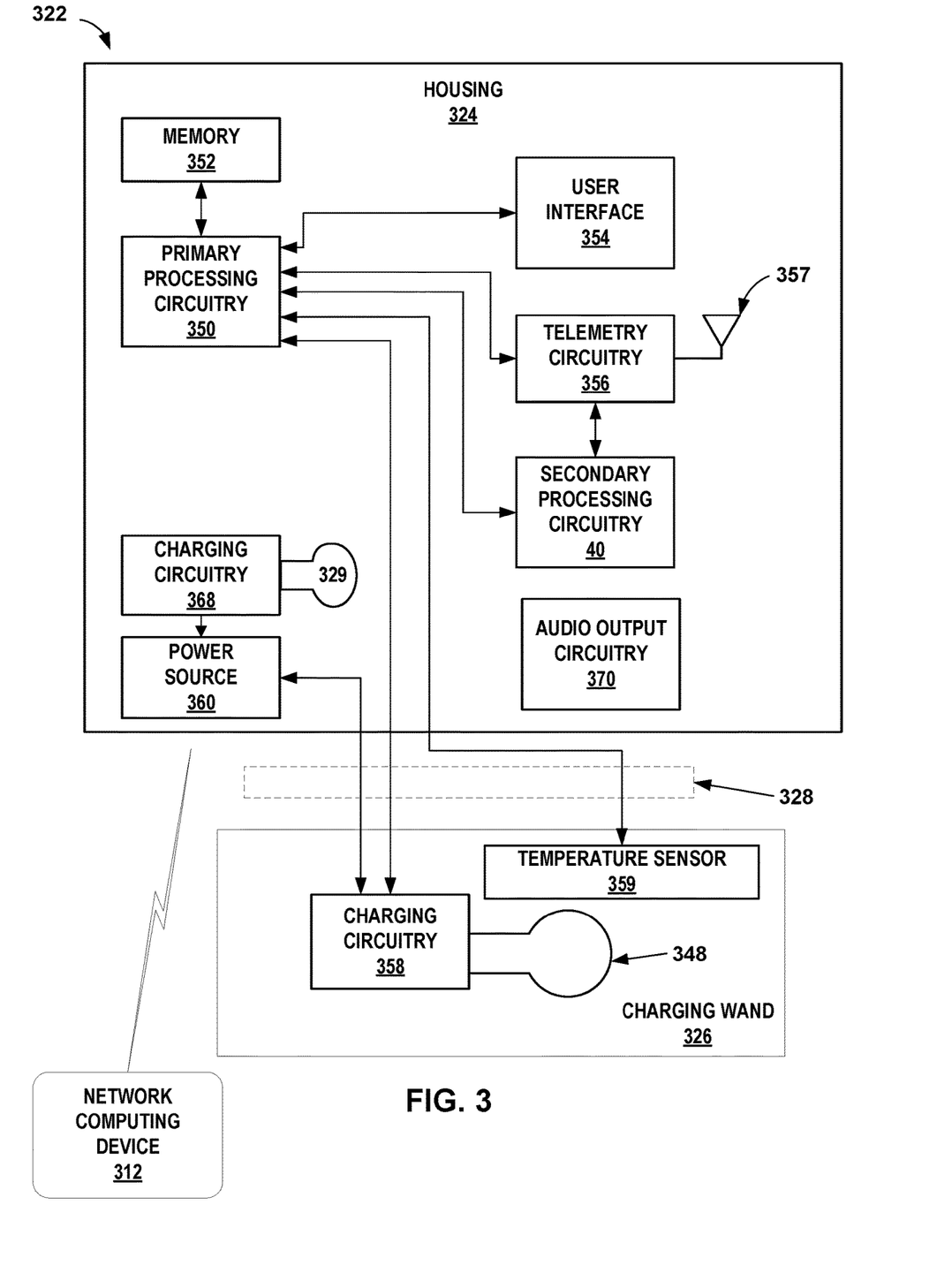
FIG. 3 is a block diagram of an example external computing device of FIG. 1.

FIG. 3 is a block diagram of an example an external computing device of FIG. 1. External charging device 322 in of FIG. 2 is an example of external computing device 150 described above in relation to FIG. 1. In some examples, external charging device 322 may be described as a hand-held device, in other examples, external charging device 322 may be a larger or a non-portable device. In addition, in other examples external charging device 322 may be included as part of an external programmer or include functionality of an external programmer. External charging device 322 may also be referred to as recharger 322, or programmer 322 in this disclosure.

As shown in the example of FIG. 3, external charging device 322 includes two separate components. Housing 324 encloses components such as a processing circuitry 350, memory 352, user interface 354, telemetry circuitry 356, audio output circuitry 370 and power source 360. Charging head 326, also called charging wand 326, may include charging circuitry 358, temperature sensor 359, and coil 348. Housing 324 is electrically coupled to charging head 326 via charging cable 328. Housing 324 may also include charging circuitry 368 and coil 329, which is an example of coil 329 described above in relation to FIG. 1.

In some examples, separate charging wand 326 may facilitate positioning of coil 348 over coil 216 of IMD 210. In some examples, charging circuitry 368 and/or coil 329 may be integrated within housing 324 in other examples, as described above in relation to FIG. 1. In other examples, recharger 322 may not include charging wand 326. Memory 352 may store instructions that, when executed by processing circuitry 350, causes processing circuitry 350 and external charging device 322 to provide the functionality ascribed to external charging device 322 throughout this disclosure, and/or any equivalents thereof. Coil 348 and coil 329 may also be referred to as an antenna.

In some examples, recharger 322 may include secondary processing circuitry 340, which may control telemetry circuitry 356, as well as perform other functions. Some other functions may include error checking of the operation of primary processing circuitry 350.

External charging device 322 may also include one or more temperature sensors, illustrated as temperature sensor 359, similar to temperature sensor 39 of FIG. 2. As shown in FIG. 3, temperature sensor 359 may be disposed within charging head 326. In other examples, one or more temperature sensors of temperature sensor 359 may be disposed within housing 324. For example, charging head 326 may include one or more temperature sensors positioned and configured to sense the temperature of coil 348 and/or a surface of the housing of charging head 326. In some examples, external charging device 322 may not include temperature sensor 359.

In general, external charging device 322 comprises any suitable arrangement of hardware, alone or in combination with software and/or firmware, to perform the techniques ascribed to external charging device 322, and processing circuitry 350, user interface 354, telemetry circuitry 356, and charging circuitry 358 of external charging device 322, and/or any equivalents thereof. In various examples, external charging device 322 may include one or more processors, such as one or more microprocessors, DSPs, ASICs, FPGAs, or any other equivalent integrated or discrete logic circuitry, as well as any combinations of such components. External charging device 322 also, in various examples, may include a memory 352, such as RAM, ROM, PROM, EPROM, EEPROM, flash memory, a hard disk, a CD-ROM, comprising executable instructions for causing the one or more processors to perform the actions attributed to them. Moreover, although processing circuitry 350, telemetry circuitry 356, charging circuitry 358, and temperature sensor 359 are described as separate modules, in some examples, processing circuitry 350, telemetry circuitry 356, charging circuitry 358, and/or temperature sensor 359 are functionally integrated. In some examples, processing circuitry 350, telemetry circuitry 356, charging circuitry 358, and/or temperature sensor 359 correspond to individual hardware units, such as ASICs, DSPs, FPGAs, or other hardware units.

Memory 352 may store instructions that, when executed by processing circuitry 350, cause processing circuitry 350 and external charging device 322 to provide the functionality ascribed to external charging device 322 throughout this disclosure, and/or any equivalents thereof. For example, memory 352 may include instructions that cause processing circuitry 350 to control the power level used to charge IMD 210 in response to the determined temperatures for the housing/external surface(s) of IMD 210, as communicated from IMD 210, or instructions for any other functionality. Memory 352 may include a record of selected power levels, sensed temperatures, determined temperatures, or any other data related to charging rechargeable power source 18, described above in relation to FIG. 2.

Processing circuitry 350 may, when requested, transmit any stored data in memory 352 to another computing device for review or further processing, such as to network computing device 312. Processing circuitry 350 may be configured to access memory, such as memory 32 of IMD 210 and/or memory 352 of external charging device 322, to retrieve information comprising instructions, formulas, programmed settings and parameters for electrical stimulation therapy, as well as determined values for one or more constants.

Network computing device 312 act as a server, such as a cloud based server, or a household server. In some examples network computing device 312 may be a tablet computer, laptop computer, desktop computer, mobile phone and so on. Network computing device 312 may include a user interface which may display outputs and accept inputs, such as the state of a patient's symptoms, as described above in relation to FIGS. 1 and 2. In this manner, a user interface of network computing device 312 may be described as being operatively coupled to processing circuitry 350 as well as to processing circuitry 230 depicted in FIG. 2.

User interface 354 may also receive user input via user interface 354. The input may be, for example, in the form of pressing a button on a keypad or selecting an icon from a touch screen. The input may change programmed settings, start or stop therapy, request starting or stopping a recharge session, a desired level of charging, or one or more statistics related to charging rechargeable power source 18 (e.g., the cumulative thermal dose). In this manner, user interface 354 may allow the user to view information related to the operation of IMD 210. As described above in relation to FIGS. 1 and 2, user interface 354 may receive an input from a user to start the procedure to balance clinical efficacy with reducing battery consumption. For each test cycle, user interface 354 may display a query to the user regarding the state of the patient's symptoms, e.g., have the patient's symptoms returned after adjusting a parameter. Processing circuitry 350 may receive the user input and determine whether to increment or decrease the ON-time or OFF-time. In some examples, processing circuitry 350 may send a programming command to the implanted device, e.g., IMD 110 or IMD 210 depicted in FIGS. 1 and 2, to adjust the ON-time or OFF-time in response to the received user input.

Charging circuitry 358 may include one or more circuits that generate an electrical signal, and an electrical current, within primary coil 348. Charging circuitry 358 may generate an alternating current of specified amplitude and frequency in some examples. In other examples, charging circuitry 358 may generate a direct current. In any case, charging circuitry 358 may be capable of generating electrical signals, and subsequent magnetic fields, to transmit various levels of power to IMD 210. In this manner, charging circuitry 358 may be configured to charge rechargeable power source 18 of IMD 210 with the selected power level.

Power source 360 may deliver operating power to the components of external charging device 322. Power source 360 may also deliver the operating power to drive primary coil 348 during the charging process. Power source 360 may include a battery and a power generation circuit to produce the operating power. In some examples, a battery of power source 360 may be rechargeable to allow extended portable operation. In other examples, power source 360 may draw power from a wired voltage source such as a consumer or commercial power outlet.

Telemetry circuitry 356 supports wireless communication between IMD 210 and external charging device 322 under the control of processing circuitry 350. Telemetry circuitry 356 may also be configured to communicate with another computing device via wireless communication techniques, or direct communication through a wired connection. In some examples, telemetry circuitry 356 may be substantially similar to telemetry circuitry 236 of IMD 210 described herein, providing wireless communication via an RF or proximal inductive medium, e.g., using coil 348. In some examples, telemetry circuitry 356 may include an antenna 357, which may take on a variety of forms, such as an internal or external antenna. Although telemetry modules 356 and 36 may each include dedicated antennas for communications between these devices, telemetry modules 356 and 36 may instead, or additionally, be configured to utilize inductive coupling from coils 216 and 348 to transfer data.

Examples of local wireless communication techniques that may be employed to facilitate communication between external charging device 322 and IMD 210 include radio frequency and/or inductive communication according to any of a variety of standard or proprietary telemetry protocols, or according to other telemetry protocols such as the IEEE 802.11× or Bluetooth specification sets. In this manner, other external devices may be capable of communicating with external charging device 322 without needing to establish a secure wireless connection.

As described above in relation to FIG. 1, processing circuitry 350 may use any one or more system metrics to determine power transfer to IMD 10. In some examples, IMD 10 may send a signal indicating an amount of current output by the recharge circuitry of IMD 10. In other examples, processing circuitry 350 may calculate other system metrics, such as alignment of coil 348 to coil 216 of IMD 10 using any of several techniques, including heat calculations, temperature measurements, detection of metal, and so on.

Figure 4:
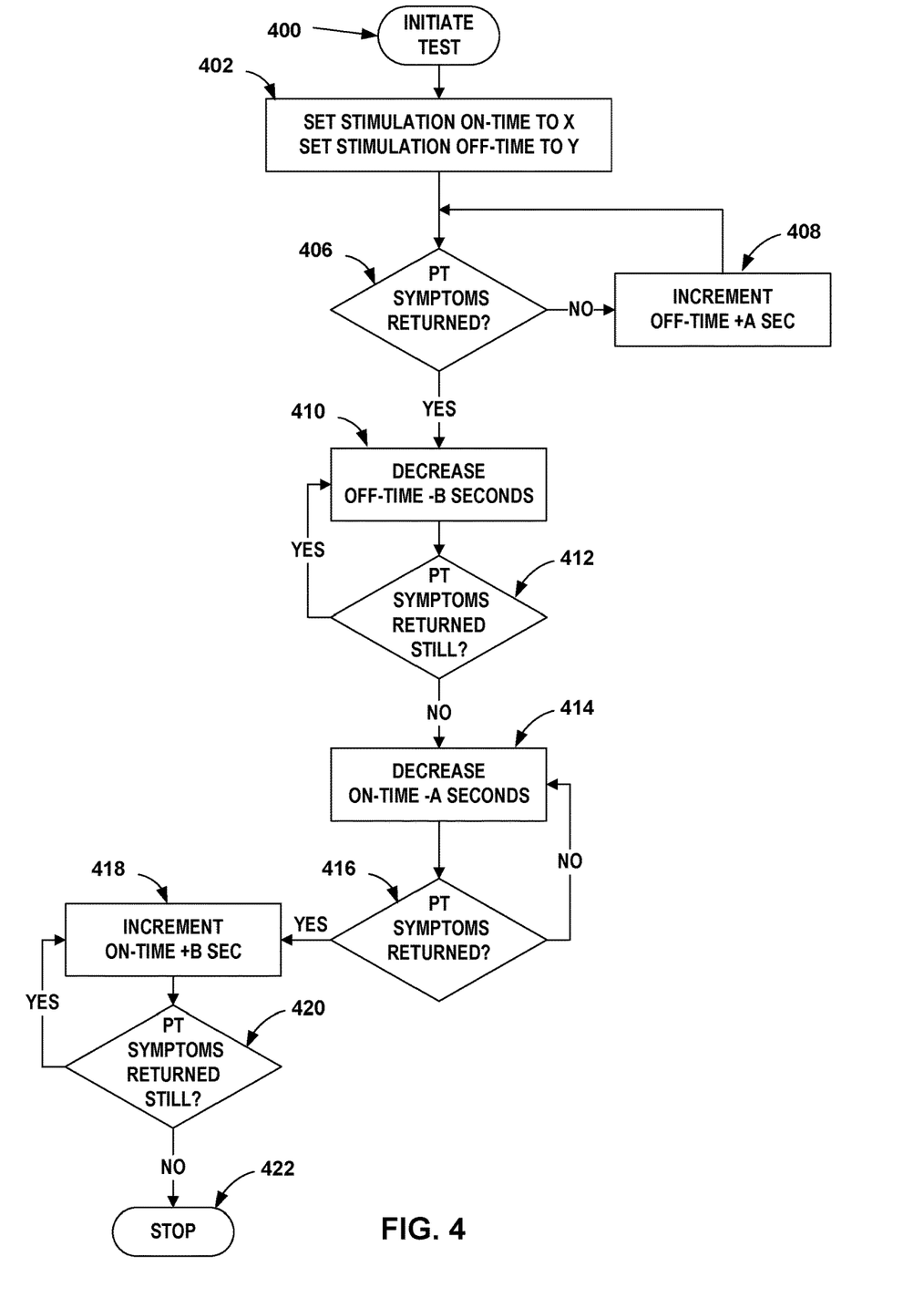
FIG. 4 is a flow chart illustrating an example operation of the medical system with the user-driven auto cycling procedure of this disclosure.

FIG. 4 is a flow chart illustrating an example operation of the medical system with the user-driven auto cycling procedure of this disclosure. The blocks shown in the example of FIG. 4 will be described in terms of FIGS. 2 and 3 and the medical system depicted in FIG. 1, which includes one or more electrical leads with one or more electrodes in contact with tissue of a patient connected to an implantable medical device.

At some time after implanting an IMD, e.g., IMD 110 or IMD 210 depicted in FIG. 1 or 2, a user may initialize the procedure of this disclosure to reduce battery power used to deliver electrical stimulation therapy while maintaining clinical efficacy to relieve the patient's symptoms. The user may start this procedure during implant recovery, during a follow-up visit and as many times during the life of the IMD as desired. Also, the example of FIG. 4 is just one possible implementation of the techniques of this disclosure. In other examples, more or fewer steps may be included, and the order of the steps may be different than shown in FIG. 4.

A user interface of system 100 may be configured to receive input from a user to start the auto cycling procedure (400), as well as receive the input describing the state of symptoms of the patient. As described above, the user interface may include user interface 354 on external computing device 322, or a user interface on a network computing device, such as a tablet computer, smart phone and so on. Primary processing circuitry 350 may receive the input to initiate the test (400) and execute programming instructions to step through the procedure.

In some examples, a health care provider may have determined the electrical stimulation therapy parameters and programmed IMD 210 with the parameters to cause the electrical stimulation circuitry to output electrical stimulation therapy to the patient. As described above, parameters may include magnitude, ON-time, OFF-time and so on. In some examples, for the auto cycling test, processing circuitry of system 100 may use the initial settings to set stimulation ON-time and set the stimulation OFF-time (402). Therefore an example ON-time of X and OFF-time of Y may be the initially selected ON-time and OFF-time set by the health care provider. In other examples, based on programming instructions, e.g., stored at memory 352, the processing circuitry may set the auto cycling ON-time of X and OFF-time of Y to values different from the initial values set by the health care provider.

In some examples, primary processing circuitry 350 of external computing device 322 may execute the steps shown in FIG. 4 and only send updated parameters to IMD 210 via communication circuitry, e.g., telemetry circuitry 356. In other examples, processing circuitry 230 of IMD 210 may execute some or most of the steps shown in FIG. 4. To simplify the description, this disclosure will assume that processing circuitry 350 will execute the programming instructions to perform the steps of the auto cycling procedure of FIG. 4.

After setting stimulation ON-time and the stimulation OFF-time (402), processing circuitry 350 may pause and wait for input describing the state of symptoms of the patient. Responsive to receiving input that the symptoms of the patient have not returned (NO branch of 406), processing circuitry 350 may increment the OFF-time by a first duration (408), e.g., increase by A seconds. In other words, processing circuitry 350 sets the OFF-time to Y+A, then pauses again waiting for input regarding the patient's symptoms.

Responsive to receiving input via the user interface that the symptoms of the patient have not returned, processing circuitry 350 may increment the OFF-time again (408) by the first duration, e.g., by another A seconds, thereby setting the OFF-time to Y+2A. Note that incrementing the OFF-time by a set, predetermined amount after each test cycle as shown in the example of FIG. 4 is only one possible implementation of the auto cycling procedure. In other examples, the incremental step may gradually increase, gradually decrease, be set based on a relationship between step size and range of values for the OFF-time parameter, and so on.

Responsive to receiving input that the symptoms of the patent have returned (YES branch of 406), processing circuitry 350 may decrease the OFF-time by a second duration (410), e.g., reduce the OFF-time parameter by B seconds. In some examples, B may be less than A, as described above, while in other examples B may the same as A. The value of the increments for A and B may be any value. Some examples may include A is five seconds while B is two seconds, A is set to 10 seconds and B is set to 10 seconds, A is thirty seconds and B is fifteen seconds, and so on.

After reducing the OFF-time, processing circuitry 350 may pause and wait to receive input via the user interface describing the state of symptoms of the patient. In some examples, after decreasing the OFF-time by the second duration, and receiving input via the user interface that the symptoms of the patient have still returned, i.e., that decreasing the OFF-time by B seconds did not relieve the patient's symptoms, then processing circuitry 350 may decrease the OFF-time again by the second duration (YES branch of 412).

After decreasing the OFF-time by the second duration and responsive to receiving input that the symptoms of the patient have not returned (NO branch of 412), processing circuitry 350 may start adjusting the ON-time parameter. Processing circuitry 350 may decrease the ON-time by a third duration (414). In the example of FIG. 4, processing circuitry 350 decreases the ON-time by A seconds, e.g., the same increment as for increasing the OFF-time. However, in other examples, the increment to decrease the ON-time may be different from the increment to increase the OFF-time.

Processing circuitry 350 may pause to receive input via the user interface describing the state of symptoms of the patient. Processing circuitry 350 may begin the next test cycle after receiving input that the symptoms of the patient have not returned (NO branch of 416), again decrease the ON-time again by the third duration (414), resulting in an ON-time of X−2A.

Processing circuitry 350 may continue to decrease the ON-time and pause until, responsive to receiving input that the symptoms of the patent have returned (YES branch of 416), processing circuitry 350 may increment the ON-time by a fourth duration (418), e.g., by B seconds. In the example of FIG. 4, the increment amount (B) after the patient symptoms have returned is the same as the decrease amount (B) shown in 410 for the OFF-time. However, in other examples, the values may be different.

After pausing to receive input via the user interface describing the state of symptoms of the patient, processing circuitry 350 may continue incrementing the ON-time by B seconds (YES branch of 420), until receiving input that the symptoms of the patient have NOT returned, e.g., the ON-time and OFF-time settings relieve the patient's symptoms (NO branch of 420). As noted above, relieving the patient's symptoms may be patient dependent and may not result in complete relief. For example, the electrical stimulation therapy may provide partial pain relief, a reduction in tremors, an improvement in gait, and so on. Once the parameters for the electrical stimulation therapy provide clinical efficacy, processing circuitry 350 may end the test procedure (422) and cause the electrical stimulation circuitry to output the electrical stimulation therapy according to the parameters, including ON-time and OFF-time.

In some examples, the steps of FIG. 4 may be performed multiple times for an IMD and a patient. For example, as the patient's conditions progress, the therapy delivery may change to provide relief. In some examples, a clinician may execute the steps of FIG. 5 during a follow up health care visit. In other examples, a clinician or other caregiver may trigger the steps of FIG. 4 remotely, such as via network computing device 312.

The techniques of this disclosure may also be described in the following examples.

Example 1: A method comprising: causing, by processing circuitry, electrical stimulation circuitry of an implantable medical device (IMD) to output electrical stimulation therapy to a patient via electrodes implanted near a target nerve of the patient, wherein the electrical stimulation therapy is defined by parameters, the parameters comprising ON-time and OFF-time; incrementing, by the processing circuitry, the OFF-time by a first duration; receiving, by the processing circuitry, input via a user interface operatively coupled to the processing circuitry, the input describing the state of symptoms of the patient, wherein the electrical stimulation therapy is configured to relieve the symptoms; responsive to receiving input that the symptoms of the patient have not returned incrementing, by the processing circuitry, the OFF-time again by the first duration; responsive to receiving input that the symptoms of the patent have returned: decreasing, by the processing circuitry, the OFF-time by a second duration; and receiving, by the processing circuitry, input via the user interface describing the state of symptoms of the patient. After decreasing the OFF-time by the second duration and responsive to receiving input that the symptoms of the patient have returned decreasing, by the processing circuitry, the OFF-time again by the second duration.

Example 2: The method of example 1, further includes after decreasing the OFF-time by the second duration and responsive to receiving input that the symptoms of the patient have not returned, decreasing, by the processing circuitry, the ON-time by a third duration; receiving, by the processing circuitry, input via the user interface describing the state of symptoms of the patient; responsive to receiving input that the symptoms of the patient have not returned decreasing again, by the processing circuitry, the ON-time again by the third duration; responsive to receiving input that the symptoms of the patent have returned: incrementing, by the processing circuitry, the ON-time by a fourth duration; and receiving, by the processing circuitry, input via the user interface describing the state of symptoms of the patient; after incrementing the ON-time by the fourth duration and responsive to receiving input that the symptoms of the patient have NOT returned, causing, by processing circuitry, the electrical stimulation circuitry to output the electrical stimulation therapy according to the parameters, including ON-time and OFF-time.

Example 3: The method of example 2, wherein the first duration is the same as the third duration.

Example 4: The method of any of examples 2 and 3, wherein the second duration is the same as the fourth duration.

Example 5: The method of any of examples 1 through 4, wherein the second duration is less than the first duration.

Example 6: A system comprising: an electrical lead including one or more electrodes in contact with tissue of a patient; a user interface configured to receive input from a user; an implantable medical device comprising: an electrical connector configured to connect to the electrical lead; electrical stimulation circuitry configured to output electrical stimulation therapy to a patient via the one or more electrodes, wherein the electrical stimulation therapy is configured to relieve symptoms of the patient. The system further includes processing circuitry configured to: cause the electrical stimulation circuitry to output electrical stimulation therapy to a patient wherein the electrical stimulation therapy is defined by parameters, the parameters comprising ON-time and OFF-time; increment the OFF-time by a first duration; receive input via the user interface, the input describing the state of symptoms of the patient; responsive to receiving input that the symptoms of the patient have not returned increment the OFF-time again by the first duration; responsive to receiving input that the symptoms of the patent have returned: decrease the OFF-time by a second duration; and receive input via the user interface describing the state of symptoms of the patient; after decreasing the OFF-time by the second duration and responsive to receiving input that the symptoms of the patient have returned decrease the OFF-time again by the second duration.

Example 7: The system of example 6, wherein the processing circuitry is further configured to: after decreasing the OFF-time by the second duration and responsive to receiving input that the symptoms of the patient have not returned, decrease the ON-time by a third duration; receive input via the user interface describing the state of symptoms of the patient; responsive to receiving input that the symptoms of the patient have not returned, again decrease the ON-time again by the third duration; responsive to receiving input that the symptoms of the patent have returned: increment the ON-time by a fourth duration; and receive input via the user interface describing the state of symptoms of the patient; after incrementing the ON-time by the fourth duration and responsive to receiving input that the symptoms of the patient have NOT returned, cause the electrical stimulation circuitry to output the electrical stimulation therapy according to the parameters, including ON-time and OFF-time.

Example 8: The system of example 7, wherein the first duration is the same as the third duration.

Example 9: The system of any of examples 7 and 8, wherein the second duration is the same as the fourth duration.

Example 10: The system of any of examples 6 through 9, wherein the second duration is less than the first duration.

Example 11: A non-transitory computer-readable storage medium comprising instructions that, when executed, cause one or more processors of a computing device to: cause electrical stimulation circuitry of an implantable medical device to output electrical stimulation therapy to a patient wherein: the electrical stimulation therapy is defined by parameters, the parameters comprising ON-time and OFF-time, and wherein the electrical stimulation therapy is configured to relieve symptoms of the patient; increment the OFF-time by a first duration; receive input via a user interface, the input describing the state of symptoms of the patient; responsive to receiving input that the symptoms of the patient have not returned increment the OFF-time again by the first duration; responsive to receiving input that the symptoms of the patent have returned: decrease the OFF-time by a second duration; and receive input via the user interface describing the state of symptoms of the patient; after decreasing the OFF-time by the second duration and responsive to receiving input that the symptoms of the patient have returned decrease the OFF-time again by the second duration.

Example 12: The non-transitory computer-readable storage medium of example 11, wherein the instructions further cause the processing circuitry to: after decreasing the OFF-time by the second duration and responsive to receiving input that the symptoms of the patient have not returned, decrease the ON-time by a third duration; receive input via the user interface describing the state of symptoms of the patient; responsive to receiving input that the symptoms of the patient have not returned, again decrease the ON-time again by the third duration; responsive to receiving input that the symptoms of the patent have returned: increment the ON-time by a fourth duration; and receive input via the user interface describing the state of symptoms of the patient; after incrementing the ON-time by the fourth duration and responsive to receiving input that the symptoms of the patient have NOT returned, cause the electrical stimulation circuitry to output the electrical stimulation therapy according to the parameters, including ON-time and OFF-time.

Various examples of the disclosure have been described. These and other examples are within the scope of the following claims.

What is claimed is:

1. A method comprising:
controlling, by processing circuitry, electrical stimulation circuitry of an implantable medical device (IMD) to deliver electrical stimulation to a patient via electrodes implanted near a target nerve of the patient, wherein the electrical stimulation is defined by parameters, the parameters comprising at least an ON-time and an OFF-time;
receiving, by the processing circuitry, input via a user interface operatively coupled to the processing circuitry, that symptoms of the patient have not returned, wherein the electrical stimulation is configured to reduce the symptoms;
responsive to receiving input that the symptoms of the patient have not returned incrementing, by the processing circuitry, the OFF-time by the first duration;
receiving, by the processing circuitry, input via a user interface that the symptoms of the patient have returned;
responsive to receiving input that the symptoms of the patent have returned:
decreasing, by the processing circuitry, the OFF-time by a second duration.

2. The method of claim 1, further comprising: after decreasing the OFF-time by the second duration and responsive to receiving input via the user interface that the symptoms of the patient have returned, decreasing, by the processing circuitry, the OFF-time again by the second duration.

3. The method of claim 1, further comprising:
after decreasing the OFF-time by the second duration and responsive to receiving input that the symptoms of the patient have not returned, decreasing, by the processing circuitry, the ON-time by a third duration;
receiving, by the processing circuitry, input via the user interface that the symptoms of the patient have not returned;
responsive to receiving input that the symptoms of the patient have not returned decreasing again, by the processing circuitry, the ON-time again by the third duration;
responsive to receiving input that the symptoms of the patent have returned:
incrementing, by the processing circuitry, the ON-time by a fourth duration; and
receiving, by the processing circuitry, input via the user interface that the symptoms of the patient have not returned; and
after incrementing the ON-time by the fourth duration and responsive to receiving input that the symptoms of the patient have NOT returned, causing, by processing circuitry, the electrical stimulation circuitry to output the electrical stimulation therapy according to the parameters, including ON-time and OFF-time.

4. The method of claim 3, wherein the first duration is the same as the third duration.

5. The method of claim 3, wherein the second duration is the same as the fourth duration.

6. The method of claim 1, wherein the second duration is less than the first duration.

7. A system comprising:
a user interface configured to receive input from a user; and
processing circuitry configured to:
control electrical stimulation circuitry to output electrical stimulation to a patient,
wherein the electrical stimulation is defined by parameters, the parameters comprising ON-time and OFF-time, and
wherein the electrical stimulation is configured to relieve symptoms of the patient;
increment the OFF-time by a first duration;
receive input via the user interface, the first input describing that the symptoms of the patient have not returned;
responsive to receiving input that the symptoms of the patient have not returned increment the OFF-time by the first duration;
receive input describing that the symptoms of the patient have returned;
responsive to receiving input that the symptoms of the patent have returned, decrease the OFF-time by a second duration.

8. The system of claim 7, the system further comprising:
an electrical lead comprising one or more electrodes in contact with tissue of the patient; and
an implantable medical device comprising:
the processing circuitry;
the electrical stimulation circuitry;
an electrical connector configured to connect the electrical stimulation circuitry to the electrical lead.

9. The system of claim 8, wherein the processing circuitry is further configured to:
receive input via the user interface that the symptoms of the patient have returned; and
after decreasing the OFF-time by the second duration and responsive to receiving input that the symptoms of the patient have returned decrease the OFF-time again by the second duration.

10. The system of claim 8, wherein the processing circuitry is further configured to:
  after decreasing the OFF-time by the second duration and responsive to receiving input that the symptoms of the patient have not returned, decrease the ON-time by a third duration;
  receive input via the user interface that the symptoms of the patient have not returned;
  responsive to receiving input that the symptoms of the patient have not returned, again decrease the ON-time again by the third duration;
  receive input via the user interface that the symptoms of the patient have returned;
  responsive to receiving input that the symptoms of the patent have returned, increment the ON-time by a fourth duration;
  receive input that the symptoms of the patient have not returned; and
  after incrementing the ON-time by the fourth duration and responsive to receiving input that the symptoms of the patient have not returned, cause the electrical stimulation circuitry to output the electrical stimulation therapy according to the parameters, including ON-time and OFF-time.

11. The system of claim 10, wherein the first duration is the same as the third duration.

12. The system of claim 10, wherein the second duration is the same as the fourth duration.

13. The system of claim 10, wherein the second duration is less than the first duration.

14. A non-transitory computer-readable storage medium comprising instructions that, when executed, cause one or more processors of a computing device to:
  control electrical stimulation circuitry of an implantable medical device to output electrical stimulation to a patient wherein:
    the electrical stimulation is defined by parameters, the parameters comprising ON-time and OFF-time, and
    the electrical stimulation is configured to relieve symptoms of the patient;
  receive input via a user interface, that the symptoms of the patient have not returned;
  responsive to receiving input that the symptoms of the patient have not returned increment the OFF-time by the first duration;
  responsive to receiving input that the symptoms of the patent have returned:
    decrease the OFF-time by a second duration.

15. The non-transitory computer-readable storage medium of claim 14, wherein the instructions further cause the processing circuitry to:
  after decreasing the OFF-time by the second duration, receive input via the user interface input that the symptoms of the patient have returned; and
  and responsive to receiving input that the symptoms of the patient have returned decrease the OFF-time again by the second duration.

16. The non-transitory computer-readable storage medium of claim 14, wherein the instructions further cause the processing circuitry to:
  after decreasing the OFF-time by the second duration and responsive to receiving input that the symptoms of the patient have not returned, decrease the ON-time by a third duration;
  receive input via the user interface that the symptoms of the patient have not returned;
  responsive to receiving input that the symptoms of the patient have not returned, again decrease the ON-time again by the third duration;
  responsive to receiving input that the symptoms of the patent have returned:
    increment the ON-time by a fourth duration; and
    receive input via the user interface describing that the symptoms of the patient have NOT returned; and
  after incrementing the ON-time by the fourth duration and responsive to receiving input that the symptoms of the patient have not returned, control the electrical stimulation circuitry to output the electrical stimulation therapy according to the parameters, including ON-time and OFF-time.

* * * * *